United States Patent
Ding et al.

(10) Patent No.: US 11,382,847 B2
(45) Date of Patent: Jul. 12, 2022

(54) HIGH POLYOL WASH COMPOSITION

(71) Applicant: Conopco, Inc., Englewood Cliffs, NJ (US)

(72) Inventors: Zhaowei Ding, Cheshire, CT (US); Kerin Frances Jacob, Orange, CT (US); Tirucherai Varahan Vasudevan, Bethany, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 16/804,856

(22) Filed: Feb. 28, 2020

(65) Prior Publication Data

US 2021/0267856 A1 Sep. 2, 2021

(51) Int. Cl.

| | |
|---|---|
| *A61K 8/34* | (2006.01) |
| *A61K 8/365* | (2006.01) |
| *A61K 8/368* | (2006.01) |
| *A61K 8/37* | (2006.01) |
| *A61K 8/42* | (2006.01) |
| *A61K 8/44* | (2006.01) |
| *A61K 8/46* | (2006.01) |
| *A61K 8/73* | (2006.01) |
| *A61K 8/81* | (2006.01) |
| *A61Q 19/10* | (2006.01) |

(52) U.S. Cl.
CPC .............. *A61K 8/345* (2013.01); *A61K 8/365* (2013.01); *A61K 8/368* (2013.01); *A61K 8/37* (2013.01); *A61K 8/42* (2013.01); *A61K 8/44* (2013.01); *A61K 8/466* (2013.01); *A61K 8/73* (2013.01); *A61K 8/8147* (2013.01); *A61K 8/8152* (2013.01); *A61Q 19/10* (2013.01); *A61K 2800/262* (2013.01); *A61K 2800/48* (2013.01)

(58) Field of Classification Search
None
See application file for complete search history.

(56) References Cited

U.S. PATENT DOCUMENTS

| | | |
|---|---|---|
| 5,009,814 A | 4/1991 | Kelkenberg et al. |
| 5,389,279 A | 2/1995 | Au et al. |
| 5,393,466 A | 2/1995 | Ilardi et al. |
| 6,444,629 B1 | 9/2002 | Elliott et al. |
| 2006/0025319 A1 | 2/2006 | Subramanian et al. |
| 2006/0025619 A1 | 2/2006 | Agoston et al. |
| 2013/0225693 A1 | 8/2013 | Walke |
| 2016/0000669 A1 | 1/2016 | Hinman et al. |
| 2016/0089314 A1 * | 3/2016 | Marsh ................ A61K 8/0208 424/401 |
| 2019/0330570 A1 * | 10/2019 | Herbst ............... C11D 3/38618 |

FOREIGN PATENT DOCUMENTS

| | | | |
|---|---|---|---|
| EP | 2057980 | 4/2014 | |
| FR | 3021531 A1 * | 12/2015 | ............ A61K 8/365 |
| GB | 2330773 | 5/1999 | |
| GB | 2421432 | 6/2006 | |
| KR | 101419508 B1 * | 7/2014 | |
| KR | 20180133170 A * | 12/2018 | |
| WO | WO2019011521 | 1/2019 | |

OTHER PUBLICATIONS

Derwent English abstract for KR 2018-0133170 A (2018).*
Derwent English abstract for FR 3 021 531 A1 (2015).*
Machine-assisted English translation for KR 101419508 B1 (2014).*
Search Report and Written Opinion in EP20167781; dated Aug. 27, 2020.

* cited by examiner

*Primary Examiner* — Sin J Lee
(74) *Attorney, Agent, or Firm* — Edward A. Squillante, Jr.

(57) ABSTRACT

The invention is directed to a stable, high polyol containing wash composition. More particularly, the invention is directed to a wash composition comprising polyol, surfactant and a gelling agent whereby the wash composition is air pocket free, has excellent moisturizing capabilities, a viscosity of 40,000 cps or less, and a slope from −0.5 to 0.0. The isotropic composition has an oil-like appearance.

16 Claims, No Drawings

HIGH POLYOL WASH COMPOSITION

FIELD OF THE INVENTION

The present invention is directed to a stable, high polyol containing wash composition. More particularly, the invention is directed to a wash composition comprising polyol, surfactant and a gelling agent whereby the wash composition has excellent moisturizing capabilities, a viscosity of 40,000 cps or less, and a slope from −0.5 to 0.0. Surprisingly, the high polyol containing wash composition is homogeneous and substantially free of air pockets, even after shaking or agitation. Such wash composition is also substantially free of oil but isotopic with an oil-like appearance.

BACKGROUND OF THE INVENTION

Personal care compositions are typically employed to cleanse skin and to reduce shine associated with sebum produced in specialized epithelial cells known as sebocytes. They are also used to minimize bacteria on the hands and face such that washing is viewed as the most effective way to prevent the spread of germs and bacteria. In fact, experts believe that periodic washing throughout the day can reduce the number of consumers catching colds by about 50%.

Consumers typically prefer compositions which are not only mild to the skin but that also deliver benefit agents to skin. Such attributes entice consumers to wash more and reduce their fears that over washing will yield dry and flaky skin by stripping the skin of important natural elements, including oils. Additionally, consumers prefer not to use products that look and feel harsh, preferring products with an attractive appearance and natural ingredients.

The present invention, therefore, is directed to a stable, high polyol containing wash composition. The composition comprises a polyol, surfactant and a gelling agent whereby the wash composition has excellent moisturizing properties, a viscosity of 40,000 cps or less, and a slope from −0.5 to 0.0. Surprisingly, the high polyol containing wash composition is homogeneous and substantially free of air pockets, even after shaking. In fact, the wash composition of the present invention is easy to apply and wash off and has an attractive oil-like and transparent or translucent appearance, notwithstanding the fact that the composition is substantially free of oil.

Additional Information

Efforts have been disclosed for making moisturizing wash compositions. In U.S. patent Application No. 2013225693, compositions with cationic surfactant and humectant are described.

Other efforts have been described for making moisturizing compositions. In GB 2330773B2, skin moisturizing preparations containing antibacterial agents are described.

Still other efforts have been described for making moisturizing compositions. In U.S. Pat. No. 6,444,629, personal cleansing compositions with good rinse feel and skin mildness are described.

None of the additional information describes a high polyol containing wash composition with superior moisturizing capabilities as claimed herein.

SUMMARY OF THE INVENTION

In a first aspect, the present invention is directed to a wash composition comprising:
a) 30 to 70% by weight polyol;
b) 0.25 to 6% by weight gelling agent;
c) 1.0 to 32% by weight surfactant; and
d) 5 to 70% by weight water,
the wash composition having a viscosity of 40,000 cps or less and a slope from −0.5 to 0.0 wherein the wash composition is transparent or translucent and is substantially free of oil and air pockets.

In a second aspect, the present invention is directed to a wash composition comprising:
a) 30 to 70% by weight polyol;
b) 0.25 to 6% by weight gelling agent;
c) 1.0 to 32% by weight surfactant;
d) 0.5 to 5.5% by weight of a mixture of glyceryl monoester and sodium benzoate at a weight ratio from 1:1 to 1:3; and
e) 5 to 70% by weight water,
the wash composition having a viscosity of 40,000 cps or less and a slope from −0.5 to 0.0 wherein the wash composition is transparent or translucent and is substantially free of oil and air pockets.

In a third aspect, the present invention is directed to a method for treating skin with the wash composition of the first or second aspect of the invention.

All other aspects of the present invention will more readily become apparent from the description and examples which follow.

Skin, as used herein, is meant to include skin on the arms (including underarms), face, feet, neck, chest, hands, legs, buttocks and scalp (including hair). High polyol containing wash composition as used herein is synonymous with "Wash Composition" and "High" means 30% or more by weight polyol in the wash composition. Shaking or agitation includes composition movement and vibration and particularly of the type associated with manufacturing, filling, shipping and the like. The wash composition of the present invention is transparent or translucent and the composition is isotropic. Substantially free of oil means no more than 2.0% by weight oil in the wash composition, and preferably no more than 1.0%, and most preferably, from 0.001 to no more than 0.5% by weight oil based on total weight of the wash composition. In an embodiment of the invention, the wash composition has no (0.0% by weight) oil. Air pockets, as used herein, means suspended air or air vacuoles or particles suspended in the isotropic wash composition of this invention. Such air pockets are visible and known to commonly have a diameter from 8 to 100 microns, more often, from 10 to 90 microns, and even more often, from 10 to 75 microns. Substantially free of air pockets means after sitting at rest for 3 to 7 days, and preferably, from over 24 to under 72 hours, and most preferably, from 12 to 24 hours the wash composition of the present invention, when visually inspected, is at least 90% free of air pockets, and preferably, at least 95% free of air pockets, and most preferably, at least 99% free of air pockets, based on volume of composition visually assessed, and even after shaking or agitation as defined herein. For the avoidance of doubt, therefore, if the wash composition is visually assessed to be 95% free of air pockets, this means the composition at rest has 95% of its volume free from any visibly suspended air. Oil-like appearance means the wash composition has the appearance of an oil-based product, like a product comprising vitamin E oil notwithstanding the fact that the product is substantially free of oil. The wash composition of the present invention is suitable to be a shampoo, make-up wash, facial wash or personal care liquid body wash. Preferably, the wash composition of the present invention is a body wash that is ready for topical application and to be wiped or washed off, and preferably, washed off, with water. The wash composition may, optionally, comprise medicinal or therapeutic agents, but preferably, is a wash which is a cosmetic and non-therapeutic wash. In an embodiment of the invention, the wash composition is a personal wash composition especially suited for use on babies. As hereinafter described, the wash composition of the present invention may optionally comprise skin benefit ingredients added thereto such as vitamins and/or derivatives thereof, resorcinols, retinoic acid precursors, colorants, moisturizers, sunscreens, mixtures thereof or the like. The skin benefit ingredients (or agents) may be water or oil soluble. If used, oil soluble skin benefit agents typically make up to 1.0% by weight of the wash composition whereby water-soluble skin benefit agents, when used, typically make up to 10% by weight of the wash composition. The wash composition typically has a pH from 4.8 to 7.5, and preferably, 5 to 7.5, and most preferably, 6.0 to 7.5. In an embodiment of the invention, the pH of the wash composition can be 6.3 to 7.2, including all ranges subsumed therein. Viscosity, unless noted otherwise, is taken with a Discovery HR-2 Rheometer using sand blasted plates having a 1000 micron gap and a first shear rate $S_A$ of 0.1 s$^{-1}$ for a first viscosity $V_A$ and a second shear rate $S_B$ of 10 s$^{-1}$ for a second viscosity $V_B$, both at 25° C. and 20 second intervals. Slope as used herein is defined as $[Log(V_B)-Log(V_A)]/[Log(S_B)-Log(S_A)]$. Viscosity is reported in Pascal seconds (1 Pascal second=1000 centipoise (cps)). Stable, as used herein, means no discoloration or phase separation of the wash composition after being stored for at least one (1) month at 45° C., preferably from 2 to 4 months at 45° C. The term comprising is meant to encompass the terms consisting essentially of and consisting of. For the avoidance of doubt, and for illustration, the composition of this invention comprising surfactant, water and polyol is meant to include a composition consisting essentially of the same and a composition consisting of the same.

Except in the operating comparative examples, or where otherwise explicitly indicated, all numbers in this description indicating amounts or ratios of materials or conditions and/or physical properties of materials and/or use are to be understood as modified by the word "about". All ranges defined herein are meant to include all ranges subsumed therein unless otherwise stated.

DETAILED DESCRIPTION OF THE INVENTION

The polyol suitable for use in the present invention is limited only to the extent that it is suitable for use in a topical composition and water soluble. Illustrative and nonlimiting examples of the polyols suitable for use in the present invention include sorbitol, glycerol, mannitol, xylitol, maltitol or mixtures thereof. In an embodiment of the invention, the polyol used is at least 50% by weight glycerol, based on total weight of the polyol used in the wash composition. In another embodiment of the invention, the polyol used is all glycerol (100% by weight). Polyol will typically make up from 30 to 70% by weight of the wash composition, and preferably, from 35 to 65% by weight of the wash composition, and most preferably, from 45 to 55% by weight of the wash composition, including all ranges subsumed therein.

As to the gelling agent used in the present invention, the same is limited only to the extent that it may be used in a composition topically applied to a consumer and suitable for use to yield a wash composition with a viscosity and slope as herein defined. Illustrative yet nonlimiting examples of the types of gelling agents suitable for use in the present invention are those classified as saccharides, acrylates, mixtures thereof or derivatives thereof. As to the polysaccharides, these include carrageenan, as well as branched polysaccharides sold under the name Tragacanth Gum, wherein the latter is a branched polysaccharide consisting of tragacanthin acid and bassorin. Tragacanthin (about 35%) is a water-soluble polysaccharide and, the main fraction, bassorin (about 65%) contains methyl ether groups and swells in water, remaining water insoluble and forming gel particles. Such Tragacanth gums are commercially available from suppliers like ISC Gums under the Tragacanth T-40E name. As to the acrylates suitable for use, these include acrylic acid crosslinked with allyl sucrose or allyl pentaerythritol acrylic acid and $C_{10}$-$C_{30}$ alkyl acrylate crosslinked with allyl pentaerythritol. Such acrylates are sold under the Carbopol® name and made commercially available by Lubrizol. Other acrylates suitable for use include those which are a copolymer formed from an ester of acrylic acid and ethoxylated palm alcohol with about 25 moles of ethylene oxide and one or more monomers of acrylic acid, methacrylic acid or one of their simple esters. These acrylates are sold, for example, under the Synthalen name, and made commercially available from suppliers like 3V.

In an embodiment of the invention, the polysaccharide is carrageenan, and in another embodiment the polysaccharide is lambda carrageenan (a D-galactose-2-sulfate and D-galactose-2,6-disulfate disaccharide). In yet another embodiment of the invention at least 50%, and preferably, at least 75%, and most preferably, at least 90% by weight of the gelling agent is lambda carrageenan based on total weight of the gelling agent in the wash composition. In a preferred embodiment of the invention, the gelling agent is one which is naturally derived and at least 95% by weight lambda carrageenan, and preferably, 100% by weight lambda carrageenan (made commercially available from suppliers like CP Kelco), based on total weight of the of gelling agent in the wash composition. Typically, the gelling agent makes up from 0.25 to 6%, and preferably, from 0.35 to 4%, and most preferably, from 0.5% to 2.5% by weight of the wash composition, including all ranges subsumed therein.

Optionally, but often preferably, glycerol monoesters are used in the wash compositions of the present invention along with a preservative, and optionally, sodium benzoate. Illustrative glycerol monoesters suitable for use in this invention include glyceryl laurate, glyceryl laurate/oleate, glyceryl adipate, glyceryl alginate, glyceryl arachidate, glyceryl behenate, glyceryl caprate, glyceryl caprylate, glyceryl hydroxystearate, mixtures thereof or the like. When used, such monoesters make up from 0.1 to 1.0%, and preferably, from 0.2 to 0.8%, and most preferably, from 0.3 to 0.7% by weight of the wash composition, and including all ranges subsumed therein. When sodium benzoate is optionally used with glycerol monoesters, the same typically makes up from 0.4 to 3%, and preferably, from 0.5 to 2.5%, and most preferably, from 0.6 to 1.5% by weight of the wash composition, including all ranges subsumed therein. In an embodiment of the invention, the weight ratio of glycerol monoester to sodium benzoate is 1:1 to 1:3, and preferably, from 1:1 to 1:2.5, and most preferably, from 1:1 to 1:2 including weight all ratios subsumed therein.

The viscosity of the wash compositions (measured at 0.1/s for 20 seconds) of the present invention is 40,000 cps or less, and preferably, from 1,500 to 30,000 cps, and most preferably, from 3,000 to 20,000 cps, including all ranges subsumed therein. The slope of wash composition is from –0.5 to 0.0, and preferably, from –0.4 to 0.0, and most preferably, –0.3 to 0.0, including all ranges subsumed therein.

As to anionic surfactants suitable for use in the wash composition of the present invention, the anionic surfactant used can include aliphatic sulfonates, such as a primary alkane (e.g., $C_8$-$C_{22}$) sulfonate, primary alkene ($C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or aromatic sulfonates such as alkyl benzene sulfonate. The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of at least 1.0, preferably less than 5, and most preferably 1 to 4, and M is a solubilizing cation such as sodium, potassium, ammonium or substituted ammonium.

The anionic may also include alkyl sulfosuccinates (including mono- and dialkyl, e.g., $C_6$-$C_{22}$ sulfosuccinates); alkyl and acyl taurates (often methyl taurates), alkyl and acyl sarcosinates, sulfoacetates, $C_8$-$C_{22}$ alkyl phosphates and phosphonates, alkyl phosphate esters and alkoxyl alkyl phosphate esters, acyl lactates, $C_8$-$C_{22}$ monoalkyl succinates and maleates, sulphoacetates, alkyl glucosides and acyl isethionates, and the like.

Sulfosuccinates may be monoalkyl sulfosuccinates having the formula:

$$R^1O_2CCH_2CH(SO_3M)CO_2M;$$

and amide-MEA sulfosuccinates of the formula:

$$R^1CONHCH_2CH_2O_2CCH_2CH(SO_3M)CO_2M \text{ wherein } R^1 \text{ ranges from } C_8\text{-}C_{22} \text{ alkyl.}$$

Sarcosinates are generally indicated by the formula:

$$R^2CON(CH_3)CH_2CO_2M, \text{ wherein } R^2 \text{ ranges from } C_8\text{-}C_{22} \text{ alkyl.}$$

Taurates are generally identified by formula:

$$R^3CONR^4CH_2CH_2SO_3M$$

wherein $R^3$ is a $C_8$-$C_{20}$ alkyl, $R^4$ is a $C_1$-$C_4$ alkyl.

M is a solubilizing cation as previously described. The isethionates that may be used include $C_8$-$C_{18}$ acyl isethionates (including those which have a substituted head group such as a $C_{1-4}$ alkyl substitution, preferably methyl substitution). These esters are prepared by a reaction between alkali metal isethionate with mixed aliphatic fatty acids having from 6 to 18 carbon atoms and an iodine value of less than 20. Often at least 75% of the mixed fatty acids have from 12 to 18 carbon atoms and up to 25% have from 6 to 10 carbon atoms.

The acyl isethionate suitable for use may be an alkoxylated isethionate such as is described in Ilardi et al., U.S. Pat. No. 5,393,466, entitled "Fatty Acid Esters of Polyalkoxylated isethonic acid; issued Feb. 28, 1995; hereby incorporated by reference. This compound has the general formula:

$$R^5C\text{—}O(O)\text{—}C(X)H\text{—}C(Y)H_2\text{—}(OCH\text{—}CH_2)_m\text{—}SO_3M$$

wherein $R^5$ is an alkyl group having 8 to 18 carbons, m is an integer from 1 to 4, X and Y are each independently hydrogen or an alkyl group having 1 to 4 carbons and M is a solubilizing cation as previously described.

In an embodiment of the invention, an anionic surfactant suitable for use is sodium lauroyl glycinate, sodium cocoyl glycinate, sodium lauroyl glutamate, sodium cocoyl glutamate, sodium lauroyl isethionate, sodium cocoyl isethionate, sodium methyl lauroyl taurate, sodium methyl cocoyl taurate or a mixture thereof. Such anionic surfactants are commercially available from suppliers like Galaxy Surfactants, Clariant, Sino Lion and Innospec. Sodium cocoyl isethionate, sodium methyl lauroyl taurate, sodium lauroyl glyconate, sodium methyl lauroyl isethionate or mixtures thereof are the preferred anionics suitable for use. In an embodiment of the invention, the anionic surfactant used is typically at least one of sodium lauroyl glutamate, sodium cocoyl isethionate, and/or sodium methyl lauroyl taurate. In a preferred embodiment, the anionic surfactant used in the wash composition of this invention is sodium lauroyl glutamate.

Amphoteric surfactants suitable for use in the invention (which depending on pH can be zwitterionic) include sodium acyl amphoacetates, sodium acyl amphopropionates, disodium acyl amphodiacetates and disodium acyl amphodipropionates where the acyl (i.e., alkanoyl group) can comprise a $C_7$-$C_{18}$ alkyl portion. Illustrative examples of the amphoteric surfactants suitable for use include sodium lauroamphoacetate, sodium cocoamphoacetate, sodium lauroamphoacetate, sodium cocoamphoacetate or mixtures thereof.

As to the zwitterionic surfactants that may be employed in the wash compositions of the present invention, such surfactants include at least one acid group. Such an acid group may be a carboxylic or a sulphonic acid group. They often include quaternary nitrogen, and therefore, can be quaternary amino acids. They should generally include an alkyl or alkenyl group of 7 to 18 carbon atoms generally comply with an overall structural formula:

$$R^6\text{—}[\text{—}C(O)\text{—}NH(CH_2)_q\text{—}]_r\text{—}N^+\text{—}(R^7\text{—})(R^8)A\text{-}B$$

where $R^7$ is alkyl or alkenyl of 7 to 18 carbon atoms; $R^7$ and $R^8$ are each independently alkyl, hydroxyalkyl or carboxyalkyl of 1 to 3 carbon atoms; q is 2 to 4; r is 0 to 1; A is alkylene of 1 to 3 carbon atoms optionally substituted with hydroxyl, and B is —$CO_2$— or —$SO_3$—.

Suitable zwitterionic surfactants that may be used in the present invention and within the above general formula include simple betaines of formula:

$$R^6\text{—}N^+\text{—}(R^7)(R^8)CH_2CO_2^-$$

and amido betaines of formula:

$$R^6\text{—}CONH(CH_2)_t\text{—}N^+\text{—}(R^7)(R^8)CH_2CO_2^- \text{ where t is 2 or 3.}$$

In both formulae $R^6$, $R^7$ and $R^8$ are as defined previously. $R^6$ may, in particular, be a mixture of $C_{12}$ and $C_{14}$ alkyl groups derived from coconut oil so that at least half, preferably at least three quarters of the groups $R^6$ have 10 to 14 carbon atoms. $R^7$ and $R^8$ are preferably methyl.

A further possibility is that the zwitterionic surfactant is a sulphobetaine of formula:

$$R^6\text{—}N^+\text{—}(R^7)(R^8)(CH_2)_3SO_3^-$$

or $$R^6\text{—}CONH(CH_2)_u\text{—}N^+\text{—}(R^7)(R^8)(CH_2)_3SO_3^-$$

where u is 2 or 3, or variants of these in which —$(CH_2)_3SO_3^-$ is replaced by —$CH_2C(OH)(H)CH_2SO_3^-$.

In these formulae, $R^6$, $R^7$ and $R^8$ are as previously defined.

Illustrative examples of the zwitterionic surfactants suitable for use include betaines like cocodimethyl carboxymethyl betaine, cocamidopropyl betaine and laurylamidopropyl betaine. An additional zwitterionic surfactant suitable for use includes cocamidopropyl sultaine. Such surfactants are made commercially available from suppliers like Stepan Company, and it is within the scope of the invention to employ mixtures of the aforementioned surfactants. In a preferred embodiment, the zwitterionic surfactant used in the wash this invention is cocamidopropyl betaine. In still another embodiment, the cocamidopropyl betaine is used with sodium lauroyl glutamate in a 1:1 to 1:5 weight ratio, and preferably, in a 1:1.1 to 1:4 ratio, and preferably, in a 1:1.2 to 1:3.5 ratio, including all weight ratios subsumed therein.

Nonionic surfactants may be used in the wash composition of the present invention. When used, nonionic surfactants are typically used at levels as low as 0.5, 1, 1.5 or 2% by weight and at levels as high as 6, 8, 10 or 12% by weight of the wash composition. The nonionics which may be used include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic surfactant compounds are alkyl ($C_6$-$C_{22}$) phenols ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other nonionic surfactants include long chain tertiary amine oxides, long chain tertiary phosphine oxides, dialkyl sulphoxides, and the like.

In an embodiment of the invention, nonionic surfactants optionally used can include fatty acid/alcohol ethoxylates having the following structures a) $HOCH_2(CH_2)_s(CH_2CH_2O)_v H$ or b) $HOOC(CH_2)_c(CH_2CH_2O)_d H$; where s and v are each independently an integer up to 18; and c and d are each independently an integer from 1 or greater. In an embodiment of the invention, s and v are each independently 6 to 18; c and d are each independently 1 to 30. Other options for nonionic surfactants include those having the formula $HOOC(CH_2)_i-CH=CH-(CH_2)_k(CH_2CH_2O)_z H$, where i, k are each independently 5 to 15; and z is 5 to 50. In another embodiment of the invention, i and k are each independently 6 to 12; and z is 15 to 35.

The nonionic may also include a sugar amide, such as a polysaccharide amide. Specifically, the surfactant may be one of the lactobionamides described in U.S. Pat. No. 5,389,279 to Au et al., entitled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

In an embodiment of the invention, cationic surfactants may optionally be used in the wash composition of the present invention.

One class of optional cationic surfactants includes heterocyclic ammonium salts such as cetyl or stearyl pyridinium chloride, alkyl amidoethyl pyrrylinodium methyl sulfate, and lapyrium chloride.

Tetra alkyl ammonium salts are another useful class of cationic surfactants suitable for optional use. Examples include cetyl or stearyl trimethyl ammonium chloride or bromide; hydrogenated palm or tallow trimethylammonium halides; behenyl trimethyl ammonium halides or methyl sulfates; decyl isononyl dimethyl ammonium halides; ditallow (or distearyl) dimethyl ammonium halides, and behenyl dimethyl ammonium chloride.

Still other types of cationic surfactants that may be used are the various ethoxylated quaternary amines and ester quats. Examples include PEG-5 stearyl ammonium lactate (e.g., Genamin KSL manufactured by Clariant), PEG-2 coco ammonium chloride, PEG-15 hydrogenated tallow ammonium chloride, PEG 15 stearyl ammonium chloride, dipalmitoyl ethyl methyl ammonium chloride, dipalmitoyl hydroxyethyl methyl sulfate, and strearyl amidopropyl dimethylamine lactate.

Even other useful cationic surfactants suitable for optional use include quaternized hydrolysates of silk, wheat, and keratin proteins, and it is within the scope of the invention to use mixtures of the aforementioned cationic surfactants.

If used, cationic surfactants will make up no more than 1.0% by weight of the wash composition. When present, they typically make up from 0.01 to 0.7%, and more typically, from 0.1 to 0.5% by weight of the wash composition, including all ranges subsumed therein.

In an embodiment of this invention, the wash composition of this invention will be substantially free of polymeric quaternary ammonium compounds (including salts of the same). In another embodiment, the wash composition will comprise less than 0.1% by weight polymeric quaternary ammonium compounds. In yet another embodiment, the wash composition comprises less than 0.01% by weight polymeric quaternary ammonium compounds. In even another embodiment, the wash composition is free of polymeric quaternary ammonium compounds (i.e., 0.0%).

Water typically makes up from 5 to 70%, and preferably, from 20 to 60%, and most preferably, from 25 to 55% by weight of the wash composition, including all ranges subsumed therein.

Adjusters suitable to modify/buffer the pH may be used. Such pH adjusters include triethylamine, NaOH, KOH, $H_2SO_4$, HCl, $C_6 H_8 O_7$ (i.e., citric acid) or mixtures thereof. The pH adjusters are added at amounts to yield the desired final pH. The pH values may be assessed with commercial instrumentation such as a pH meter made commercially available from Thermo Scientific®.

Optional skin benefit agents suitable for use in the wash composition of this invention are limited only to the extent that they are capable of being topically applied, and suitable to dissolve in the wash composition at the desired pH.

Illustrative examples of the benefit agents suitable to include in the water portion of the wash composition are acids, like amino acids, such as arginine, valine or histidine. Additional water soluble benefit agents suitable for use include vitamin $B_2$, niacinamide (vitamin $B_3$), vitamin $B_6$, vitamin C, mixtures thereof or the like. Water soluble derivatives of such vitamins may also be employed. For instance, vitamin C derivatives such as ascorbyl tetraisopalmitate, magnesium ascorbyl phosphate and ascorbyl glycoside may be used alone or in combination with each other. Other water soluble benefit agents suitable for use include 4-ethyl resorcinol, extracts like sage, aloe vera, green tea, grapeseed, thyme, chamomile, yarrow, cucumber, liquorice, rosemary extract or mixtures thereof. Water soluble sunscreens like ensulizole may also be used. Total amount of optional water soluble benefit agents (including mixtures) when present in the invention may range from 0.0 to 10%, preferably from 0.001 to 8%, and most preferably, from 0.01 to 6% by weight, based on total weight of the wash composition and including all ranges subsumed therein.

It is also within the scope of the present invention to optionally include oil (i.e., non-water) soluble benefit agents. The wash composition, again, is substantially free of oil, and preferably, has no oil (0.0%) where oil is not meant to include any oil added from a fragrance. Thus, oil soluble actives or benefit agents are solubilized in the surfactants used. The only limitation with respect to such oil soluble benefit agents are that the same are suitable to provide a benefit when topically applied.

Illustrative examples of the types of oil soluble benefit agents that may optionally be used in the compositions of this invention include components like stearic acid, vitamins like Vitamin A, D, E and K (and their oil soluble derivatives), sunscreens like ethylhexylmethoxycinnamate, bisethyl hexyloxyphenol methoxyphenol triazine, 2-ethylhexyl-2-cyano-3,3-diphenyl-2-propanoic acid, drometrizole trisiloxane, 3,3,5-trimethyl cyclohexyl 2-hydroxybenzoate, 2-ethylhexyl-2-hydroxybenzoate or mixtures thereof.

Other optional oil soluble benefit agents suitable for use include resorcinols like 4-hexyl resorcinol, 4-phenylethyl resorcinol, 4-cyclopentyl resorcinol, 4-cyclohexyl resorcinol 4-isopropyl resorcinol or a mixture thereof. Also, 5-substituted resorcinols like 4-cyclohexyl-5-methylbenzene-1,3-diol, 4-isopropyl-5-methylbenzene-1,3-diol, mixtures thereof or the like may be used. The 5-substituted resorcinols, and their synthesis are described in commonly assigned U.S. Published Patent Application No. 2016/0000669A1.

Even other oil soluble actives suitable for use include omega-3 fatty acids, omega-6 fatty acids, climbazole, farnesol, ursolic acid, myristic acid, geranyl geraniol, oleyl betaine, cocoyl hydroxyethyl imidazoline, hexanoyl sphingosine, 12-hydroxystearic acid, petroselinic acid, conjugated linoleic acid, terpineol, thymol mixtures thereof or the like.

In an embodiment of the invention, the optional oil soluble benefit agent used is a retinoic acid precursor. In one embodiment of the invention, the retinoic acid precursor is retinol, retinal, retinyl propionate, retinyl palmitate, retinyl acetate or a mixture thereof. Retinyl propionate, retinyl palmitate and mixtures thereof are typically preferred.

Still another retinoic acid precursor suitable for use is hydroxyanasatil retinoate made commercially available under the name Retextra as supplied by Molecular Design International. The same may be used in a mixture with the oil soluble actives described herein.

When optional oil soluble active is used in the compositions of the invention, such active typically makes up from 0.0 to 0.75%, and preferably, from 0.001 to 5%, and most preferably, from 0.05 to 0.35% by weight of the wash composition. In yet another embodiment, oil makes up from 0.1 to 0.5% by weight of the total weight of the wash composition, including all ranges subsumed therein and excluding any oil provided from a fragrance.

Conventional preservatives can desirably be incorporated into the wash composition to protect against the growth of potentially harmful microorganisms, in addition to the use of sodium benzoate with glyceryl monoester as previously described. Cosmetic chemists are familiar with appropriate preservatives and routinely choose them to satisfy the preservative challenge test and to provide product stability. Suitable traditional preservatives for use include hydantoin derivatives and propionate salts. Particularly preferred preservatives are iodopropynyl butyl carbamate, phenoxyethanol, 1,2-octanediol, hydroxyacetophenone, ethylhexylglycerine, hexylene glycol, methyl paraben, propyl paraben, imidazolidinyl urea, sodium dehydroacetate, dimethyl-dimethyl (DMDM) hydantoin and benzyl alcohol and mixtures thereof. Other preservatives suitable for use include sodium dehydroacetate, chlorophenesin and decylene glycol. The preservatives should be selected having regard for the use of the composition and possible incompatibilities between the preservatives and other ingredients in the emulsion. Preservatives are preferably employed in amounts ranging from 0.01% to 2.0% by weight of the total weight of the wash composition, including all ranges subsumed therein. Also preferred is a preservative system with hydroxyacetophenone alone or in a mixture with other preservatives.

Fragrances, fixatives, chelators (like EDTA) and exfoliants may optionally be included in the wash composition of the present invention. Each of these substances may range from about 0.03 to about 5%, preferably between 0.1 and 3% by weight of the total weight of the wash composition, including all ranges subsumed therein. To the extent the exfoliants are used, those selected should be of small enough particle size so that they do not impede the performance of any packaging used to dispense the compositions of this invention.

Conventional emulsifiers having an HLB of greater than 8 may optionally be used. Illustrative examples include Tween, 40, 60, 80, polysorbate 20 and mixtures thereof. Typically, emulsifiers for water continuous systems make up from 0.03 to 1.5% by weight of the wash composition.

As to the wash composition of the present invention, the same typically has from 1 to 32%, and preferably, from 2 to 20%, and most preferably, from 3 to 12% by weight total surfactant, based on total weight of the wash composition and including all ranges subsumed therein. In an embodiment of the invention, the wash composition comprises from 7 to 11% by weight total surfactant based on total weight of the wash composition and including all ranges subsumed therein.

When making wash composition of the present invention, the desired ingredients may be mixed with conventional apparatus under moderate shear and atmospheric conditions, with temperature being from 30 to 85° C. whereby shear continues until a homogeneous product is recovered.

The packaging for the wash composition typically is not limited as long as composition can be dispensed. In an embodiment on the invention, the wash composition is sold in a pouch, bottle, jar, tube or canister. The packaging preferably allows for infinite numbers of refilling to invariably reduce plastic waste in the environment.

The Examples are provided to facilitate an understanding of the invention. They are not intended to limit the scope of the claims.

All Samples in the Examples were prepared by mixing the ingredients with moderate shear and with temperature being about 80° C. and pressure being atmospheric.

Example 1

| | | COMPARATIVE SAMPLES | | | | | |
|---|---|---|---|---|---|---|---|
| Ingredient Name | Purity (%) | Sample 1 % Active | Sample 2 % Active | Sample 3 % Active | Sample 4 % Active | Sample 5 % Active | Sample 6 % Active |
| Glycerin | 100 | 50 | 50 | 50 | 50 | 50 | 50 |
| Water | 100 | balance | balance | balance | balance | balance | balance |
| Iota Carrageenan | 100 | | | | | 0.4 | 1.2 |
| Kappa Carrageenan | 100 | | | | 1.2 | | |
| Xanthan Gum | 100 | 0.5 | 1.2 | 0.5 | | | |

-continued

COMPARATIVE SAMPLES

| Ingredient Name | Purity (%) | Sample 1 % Active | Sample 2 % Active | Sample 3 % Active | Sample 4 % Active | Sample 5 % Active | Sample 6 % Active |
|---|---|---|---|---|---|---|---|
| Sodium Lauroyl Glutamate[a] | 23 | 7.6 | 7.6 | | 7.6 | 7.6 | 7.6 |
| Cocamidopropyl Betaine[b] | 30 | 2.3 | 2.3 | 6.4 | 2.3 | 2.3 | 2.3 |
| Sodium Cocoyl Isethionate[c] | 84 | | | 1.6 | | | |
| Sodium Methyl Lauroyl Taurate[d] | 90 | | | 1.6 | | | |
| Stearic Acid | 100 | 0.05 | 0.05 | 0.05 | 0.05 | 0.05 | 0.05 |
| Lauric Acid | 100 | | | 0.15 | | | |
| Citric Acid Monohydrate | 100 | 0.7 | 0.7 | | 0.7 | 0.7 | 0.7 |
| Glyceryl Caprylate | 100 | 0.5 | 0.5 | | 0.5 | 0.5 | 0.5 |
| Preservatives | 100 | 0.9 | 0.9 | 0.8 | 0.9 | 0.9 | 0.9 |
| Fragrance | 100 | 0.7 | 0.7 | 1.0 | 0.4 | 0.4 | 0.4 |
| Total | | 100 | 100 | 100 | 100 | 100 | 100 |
| Total Active Surfactant | | 9.9 | 9.9 | 9.6 | 9.9 | 9.9 | 9.9 |
| Viscosity at 0.1/s (Pa*S) | | 38.4 | 398.5 | 19.4 | ND | 22.8 | 503.0 |
| Log Slope* of 0.1/s to 10/s | | −0.77 | −0.93 | −0.66 | ND | −0.70 | −0.82 |

[a] 70% Water, 3% Sodium Chloride & minors
[b] 65% Water, 4.5% Sodium Chloride & minors
[c] 15% Water and minors
[d] 9% Water and minors
[e] Pa*S × 1000 = centipoise (CPS)
ND—Not determinable, formula not stable The viscosities and slopes of the wash compositions of Samples 1-6 reflect that the same were not prepared consistent with the present invention. Moreover, the compositions were not translucent or transparent and had very visible signs of air pockets after production and filling into glass jars. The compositions were heavily aerated and after about 24 hours the air did not dissipate. The compositions of these Samples were presented to skilled panelist and none concluded the samples had an oil-like appearance.

Example 2

The compositions made in Samples 7 to 15 had viscosities and slopes to reflect they were prepared consistent with the present invention. Subsequent to preparing, the wash compositions of the Samples were transparent and substantially free (after visual inspection) of air pockets.

After moving the composition and filling glass jars, the wash compositions had visual signs of air pockets that almost completely dissipated in about 24 hours. Moreover, skilled panelists observed the compositions of Samples 7 to 15 and all concluded the compositions had an oil-like appearance, notwithstanding the fact that they were not formulated to contain oil.

INVENTIVE SAMPLES

| Ingredient Name | Purity (%) | Sample 7 % Active | Sample 8 % Active | Sample 9 % Active | Sample 10 % Active | Sample 11 % Active | Sample 12 % Active | Sample 13 % Active | Sample 14 % Active | Sample 15 % Active |
|---|---|---|---|---|---|---|---|---|---|---|
| Glycerin | 100 | 50 | 30 | 50 | 50 | 50 | 50 | 30 | 65 | 50 |
| Water | 100 | balance | balance | balance | balance | balance | balance | balance | balance | balance |
| Lambda Carrageenan | 100 | 1.2 | 1.2 | 1.2 | | | 2 | 1.3 | 1 | |
| Tragacanth Gum | 100 | | | | 0.6 | | | | | 1.2 |
| Acrylates/Palmeth-25 Acrylate Copolymer | 30 | | | | | 1.6 | | | | |
| Sodium Lauroyl Glutamate[a] | 23 | 7.6 | 7.6 | 6.5 | 7.6 | 7.6 | 7.6 | 9.2 | 3.5 | 7.6 |
| Cocamidopropyl Betaine[b] | 30 | 2.3 | 2.3 | 2.0 | 2.3 | 2.3 | 2.3 | 6 | 3 | 2.3 |
| Stearic Acid | 100 | 0.05 | 0.05 | 0.05 | 0.05 | 0.05 | 0.05 | 0.05 | 0.05 | 0.05 |
| Citric Acid Monohydrate | 100 | 0.7 | 0.7 | 0.7 | 0.7 | 0.7 | 0.7 | 0.8 | 0.4 | 0.7 |
| Glyceryl Caprylate | 100 | 0.5 | 0.5 | 0.5 | 0.5 | 0.5 | 0.5 | 0.5 | 0.5 | 0.5 |
| Preservatives | 100 | 0.9 | 0.9 | 0.9 | 0.9 | 0.9 | 0.9 | 0.9 | 0.9 | 0.9 |
| Fragrance | 100 | 0.65 | 0.65 | 0.42 | 0.42 | 0.42 | 0.42 | 0.3 | 0.3 | 0.42 |
| Total | | 100 | 100 | 100 | 100 | 100 | 100 | 100 | 100 | 100 |
| Total Active Surfactant | | 9.9 | 9.9 | 8.4 | 9.9 | 9.9 | 9.9 | 15.2 | 6.5 | 9.9 |
| Viscosity at 0.1/s (Pa*S)[e] | | 3.5 | 4.7 | 13.3 | 6.6 | 5.9 | 39.8 | 3.6 | 10.6 | 3.3 |
| Log Slope* of 0.1/s to 10/s | | −0.22 | −0.32 | −0.43 | −0.28 | −0.35 | −0.44 | −0.28 | −0.34 | −0.09 |

[a] 70% Water, 3% Sodium Chloride & minors
[b] 65% Water, 4.5% Sodium Chloride & minors
[e] Pa*S × 1000 = centipoise (CPS)

Example 3

| Ingredient | Added % by Weight |
|---|---|
| Glycerin | 50 |
| Water | 49 |
| Gum/Polymer | 1 |
| Total | 100 |

| Gelling Agent | (Weight %) | Log Slope of 0.1/s to 10/s |
|---|---|---|
| Lambda Carrageenan | 1 | −0.057 |
| Iota Carrageenan | 1 | −0.599 |
| Kappa Carrageenan | 1 | ND |
| Xanthan Gum | 1 | −0.876 |
| Tragacanth Gum | 1 | −0.621 |
| Acrylates/Palmeth-25 Acrylate Copolymer | 1 | −0.774 |

ND—not determinable, formula not stable The data demonstrates that the slope values generated for gelling agent in solvent are not indicative of performance in a wash composition, confirming that the wash compositions of the present invention are unexpectedly superior in that they are substantially air pocket free and have an oil-like appearance even when formulated free of oil.

What is claimed is:

1. A wash composition comprising:
   a) 30 to 70% by weight polyol;
   b) 0.25 to 6% by weight gelling agent;
   c) 1.0 to 32% by weight surfactant; and
   d) 20 to 60% by weight water,
   the wash composition having a viscosity of 40,000 cps or less and a slope from −0.5 to 0.0, wherein the wash composition is transparent or translucent and is substantially free of oil and air pockets, and further wherein the surfactant comprises cocamidopropyl betaine and sodium lauroyl glutamate in a 1:1 to 1:5 weight ratio, the viscosity taken with a Discovery HR-2 Rheometer using sand blasted plates having a 1000 micron gap and a first shear rate $S_A$ of $0.1\ s^{-1}$ for a first viscosity $V_A$ and a second shear rate of $S_B$ of $10\ s^{-1}$ for a second viscosity $V_B$, both at 25° C. and 20 second intervals and slope is $[Log(V_B)-Log(V_A)]/[Log(S_B)-Log(S_A)]$.

2. The wash composition according to claim 1, wherein the polyol is sorbitol, glycerol, mannitol, xylitol, maltitol or a mixture thereof.

3. The wash composition according to claim 1, wherein the gelling agent is an acrylate, polysaccharide or a mixture thereof.

4. The wash composition according to claim 1, wherein the gelling agent is Tragacanth Gum, lambda carrageenan, $C_{10}$-$C_{30}$ alkyl acrylate crosslinked with allyl pentaerythritol or a mixture thereof.

5. The wash composition according to claim 1, wherein the gelling agent is lambda carrageenan and the polyol is glycerol and further wherein the lambda carrageenan is present at an amount from 0.35 to 4% by weight and the glycerol is present in an amount from 35 to 65% by weight.

6. The wash composition according to claim 1, wherein the surfactant is a mixture of cocamidopropyl betaine and sodium lauroyl glutamate in a 1:1.1 to 1:4 weight ratio.

7. The wash composition according to claim 1, wherein the wash composition is isotropic.

8. The wash composition according to claim 1, wherein the wash composition is translucent.

9. The wash composition according to claim 1, wherein the composition comprises 0.5 to 5.5% by weight of a mixture of glyceryl monoester and sodium benzoate at a weight ratio from 1:1 to 1:2.5, from 35 to 60% by weight water and a viscosity from 3,000 to 20,000 cps.

10. The wash composition according to claim 9, wherein the glycerol monoester is glyceryl caprylate.

11. A method for washing skin comprising steps of contacting the skin in need of washing with the composition of claim 1 and washing off the composition with water.

12. The wash composition according to claim 1, wherein the wash composition comprises no more than 1.0% by weight oil.

13. The wash composition according to claim 1, wherein the surfactant makes up from 2 to 20% by weight of the composition.

14. The wash composition according to claim 1, wherein the surfactant makes up from 3 to 12% by weight of the composition.

15. The wash composition according to claim 1, wherein the polyol makes up from 45 to 55% by weight of the composition and the polyol comprises glycerol.

16. A wash composition comprising:
   a) 30 to 70% by weight polyol;
   b) 0.25 to 6% by weight gelling agent;
   c) 1.0 to 32% by weight surfactant;
   d) 0.5 to 5.0% by weight of a mixture of glyceryl monoester and sodium benzoate at a weight ratio from 1:1 to 1:3; and
   e) 20 to 60% by weight water,
   the wash composition having a viscosity of 40,000 cps or less and a slope from −0.5 to 0.0, wherein the wash composition is transparent or translucent and is substantially free of air pockets, and further wherein the surfactant comprises cocamidopropyl betaine and sodium lauroyl glutamate in a 1:1.2 to 1:3.5 weight ratio and the wash composition comprises no more than 1% by weight oil, the viscosity taken with a Discovery HR-2 Rheometer using sand blasted plates having a 1000 micron gap and a first shear rate $S_A$ of $0.1\ s^{-1}$ for a first viscosity $V_A$ and a second shear rate $S_B$ of $10\ s^{-1}$ for a second viscosity $V_B$, both at 25° C. and 20 second intervals and slope is $[Log(V_B)-Log(V_A)]/[Log(S_B)-Log(S_A)]$.

* * * * *